(12) United States Patent
Kobla et al.

(10) Patent No.: US 8,514,236 B2
(45) Date of Patent: Aug. 20, 2013

(54) SYSTEM AND METHOD FOR ANIMAL GAIT CHARACTERIZATION FROM BOTTOM VIEW USING VIDEO ANALYSIS

(75) Inventors: Vikrant Kobla, Ashburn, VA (US); Yiqing Liang, Vienna, VA (US); Feng-Feng Wang, Potomac, MD (US); Yi Zhang, Fairfax, VA (US)

(73) Assignee: Cleversys, Inc., Reston, VA (US)

( * ) Notice: Subject to any disclaimer, the term of this patent is extended or adjusted under 35 U.S.C. 154(b) by 2366 days.

(21) Appl. No.: 10/955,661

(22) Filed: Sep. 30, 2004

(65) Prior Publication Data

US 2007/0229522 A1    Oct. 4, 2007

Related U.S. Application Data

(63) Continuation-in-part of application No. 09/718,374, filed on Nov. 24, 2000, now Pat. No. 6,678,413.

(51) Int. Cl.
*G09G 5/36* (2006.01)

(52) U.S. Cl.
USPC .......................................................... 345/547

(58) Field of Classification Search
USPC .......................................................... 345/547
See application file for complete search history.

(56) References Cited

U.S. PATENT DOCUMENTS

| | | |
|---|---|---|
| 3,100,473 A | 8/1963 | Kissel |
| 3,304,911 A | 2/1967 | Hakata et al. |
| 3,485,213 A | 12/1969 | Scanlon |
| 3,803,571 A | 4/1974 | Luz |
| 3,974,798 A | 8/1976 | Meetze, Jr. |

(Continued)

FOREIGN PATENT DOCUMENTS

| | | |
|---|---|---|
| EP | 363755 A2 | 4/1990 |
| JP | 63-1 33061 | 6/1988 |

(Continued)

OTHER PUBLICATIONS

AccuScan on-line catalog, Nov. 19, 1997.

(Continued)

*Primary Examiner* — Anner Holder
(74) *Attorney, Agent, or Firm* — Alston & Bird LLP

(57) ABSTRACT

In general, the present invention is directed to systems and methods for finding the gait parameters of an animal using video. The invention includes a system with a video camera coupled to a computer in which the computer is configured to automatically provide animal segmentation, foot identification, foot tracking, and gait parameter calculation. In a preferred embodiment, the present invention may use a treadmill apparatus with a transparent tread or belt for gait parameter calculation. A camera may be placed directly underneath the transparent tread such that the bottom view of the animal walking or running on the transparent tread is captured by the camera. A tilted mirror may also be placed directly underneath the transparent tread in order to reflect the bottom view images to the side where they are captured by a high-speed camera. Thus, the present invention is capable of automatically monitoring a video image to identify, track and classify the actions of various animals' feet within the image. The image may be provided in real time or from storage. The invention is particularly useful for monitoring and characterizing gait behavior such as walking and running behavior and their patterns for assessing neurological functions, testing drugs and genetic mutations, but may be used in any of a number of other monitoring and surveillance applications.

44 Claims, 13 Drawing Sheets

(56) References Cited

U.S. PATENT DOCUMENTS

| | | | |
|---|---|---|---|
| 4,337,726 | A | 7/1982 | CzekaJewski et al. |
| 4,574,734 | A | 3/1986 | Mandalaywala et al. |
| 4,600,016 | A | 7/1986 | Boyd et al. |
| 4,631,676 | A | 12/1986 | Pugh |
| 4,888,703 | A | 12/1989 | Baba et al. |
| 5,299,454 | A | 4/1994 | Fuglewicz et al. |
| 5,428,723 | A | 6/1995 | Ainscow et al. |
| 5,546,439 | A | 8/1996 | Hsieh |
| 5,581,276 | A | 12/1996 | Cipolla et al. |
| 5,596,994 | A | 1/1997 | Bro |
| 5,708,767 | A | 1/1998 | Yeo et al. |
| 5,748,775 | A | 5/1998 | Tsuchikawa et al. |
| 5,816,256 | A | 10/1998 | Kissinger et al. |
| 5,821,945 | A | 10/1998 | Yeo et al. |
| 5,870,138 | A | 2/1999 | Smith et al. |
| 6,010,465 | A * | 1/2000 | Nashner .......................... 600/595 |
| 6,061,088 | A | 5/2000 | Khosravi et al. |
| 6,072,496 | A | 6/2000 | Guenter et al. |
| 6,072,903 | A | 6/2000 | Maki et al. |
| 6,081,607 | A | 6/2000 | Mori et al. |
| 6,088,468 | A | 7/2000 | Ito et al. |
| 6,144,366 | A | 11/2000 | Numazaki et al. |
| 6,212,510 | B1 | 4/2001 | Brand |
| 6,231,527 | B1 | 5/2001 | Sol |
| 6,242,456 | B1 | 6/2001 | Shuster et al. |
| 6,263,088 | B1 | 7/2001 | Crabtree et al. |
| 6,295,367 | B1 | 9/2001 | Crabtree et al. |
| 6,311,644 | B1 | 11/2001 | Pugh |
| 6,468,998 | B1 * | 10/2002 | Kuroita et al. ........... 514/214.03 |
| 6,535,131 | B1 | 3/2003 | Bar-Shalom et al. |
| 6,576,237 | B1 | 6/2003 | Ingham et al. |
| 6,601,010 | B1 | 7/2003 | Fowler et al. |
| 6,630,148 | B1 | 10/2003 | Ingham et al. |
| 6,630,347 | B1 | 10/2003 | Huang et al. |
| 6,650,778 | B1 | 11/2003 | Matsugu et al. |
| 6,678,413 | B1 | 1/2004 | Liang et al. |
| 6,704,502 | B2 | 3/2004 | Morofuji |
| 6,715,444 | B1 | 4/2004 | Yabusaki et al. |
| 6,757,444 | B2 | 6/2004 | Matsugu et al. |
| 6,819,796 | B2 * | 11/2004 | Hong et al. ................... 382/173 |
| 6,837,184 | B2 | 1/2005 | Gondhalekar et al. |
| 6,899,686 | B2 * | 5/2005 | Hampton et al. ............. 600/595 |
| 6,941,239 | B2 | 9/2005 | Unuma et al. |
| 7,133,537 | B1 | 11/2006 | Reid |
| 7,269,516 | B2 | 9/2007 | Brunner et al. |
| 2003/0024482 | A1 | 2/2003 | Gondhalekar et al. |
| 2003/0100998 | A2 * | 5/2003 | Brunner et al. .................. 702/19 |
| 2004/0009845 | A1 * | 1/2004 | Johnson .......................... 482/41 |
| 2004/0020443 | A1 | 2/2004 | Ohl |
| 2004/0141636 | A1 | 7/2004 | Liang et al. |

FOREIGN PATENT DOCUMENTS

| | | |
|---|---|---|
| JP | 08-063603 | 3/1996 |
| JP | 08-240830 | 9/1996 |
| JP | 09-073541 | 3/1997 |
| JP | 09-251441 | 9/1997 |
| JP | 11-052215 | 2/1999 |
| JP | 11-259643 | 9/1999 |
| JP | 11-296651 | 10/1999 |
| JP | 2000-215319 | 8/2000 |
| WO | WO/02/43352 | 5/2005 |

OTHER PUBLICATIONS

Allen, William H. "Animals and their Models do their Locomotions: Biologists Probe Mechanics and Energetics of Animal Motion". Jun. 1995. Biosciences. vol. 45, No. 6, pp. 381-383.

Automated Plus Maze Open/Closed Arm System; AccuScan Instruments, Inc., 1991.

Birch et al. 2001. "A miniature Hybrid Robot Propelled by Legs". Proceedings of the 2001 IEE/RSJ International Conference on Intelligent Robots and Systems, p. 845-851.

Clarke, K.A. and J. Still "Development and consistency of gait in the mouse" Physiology & Behavior 73:159-164 (2001).

Clarke, K.A. and J. Still "Gait Analysis in the Mouse" Physiology & Behavior 66(5):723-729 (1999).

Cohen, J.J. et al.; "Behavior, Stress, and Lymphocyte Recirculation"; Stress, Immunity and Aging; 1984; pp. 73-80.

Coussons-Read, Mary E. et al.; "Behavioral Assessment of the Ts65Dn Mouse, A Model for Down Syndrome: Altered Behavior In The Elevated Plus Maze and Open Field"; Behavior Genetics; vol. 26; No. 1; 1996; pp. 7-13.

Crnic, L.S. et al.; "Animal Models of Mental Retardation: An Overview"; Mental Retardation and Developmental Disabilities Research Reviews; vol. 2; 1996; pp. 185-187.

Crnic, L.S. et al.; "Animal Modes of Human Behavior: Their Application to the Study of Attachment"; The Development of Attachment and Affiliative Systems: Neurobiological and Psychobiological Aspects, Plenum, New York; 1982; pp. 31-42.

Crnic, L.S. et al.; "Behavioral Effects of Mouse Interferons-.alpha. and -.gamma. And Human Interferon-.alpha. In Mice"; Brain Research; vol. 590; 1992; pp. 277-284.

Crnic, L.S. et al.; "Behavioral Effects of Neonatal Herpes Simplex Type 1 Infection of Mice"; Neurotoxicology and Teratology; vol. 10; 1988; pp. 381-386.

Crnic, L.S. et al.; "Down Syndrome: Neuropsychology and Animal Models"; Progress in Infancy Research; vol. 1; 2000; pp. 69-111.

Crnic, L.S. et al.; "Prostaglandins Do Not Mediate Interferon-.alpha. Effects on Mouse Behavior"; Physiology & Behavior; vol. 51; 1992; pp. 349-352.

Crnic, L.S. et al.; "Separation-Induced Early Malnutrition: Maternal, Physiological and Behavioral Effects"; Physiology & Behavior; vol. 26; 1981; pp. 695-706.

Crnic, L.S.; "Animal Models of Early Malnutrition: A Comment on Bias, Dependability, and Human Importance"; Malnutrition and Behavior: Critical Assessment of Key Issues; 1984; pp. 460-468.

Crnic, L.S.; "Behavioral Consequences of Virus Infection"; Psychoneuroimmunology, Second Edition; Academic Press; 1991; pp. 749-769.

Crnic, L.S.; "Early Experience Effects: Evidence for Continuity?"; Continuities and Discontinuities in Development, Plenum Press, New York; 1984; pp. 355-368.

Crnic, L.S.; "Effects of Infantile Undernutrition on Adult Learning in Rats: Methodological and Design Problems"; Psychological Bullentin; vol. 83; No. 4; 1976; pp. 715-728.

Crnic, L.S.; "Effects of Infantile Undernutrition on Adult Sucrose Solution Consumption in the Rat"; Physiology & Behavior; vol. 22; 1979; pp. 1025-1028.

Crnic, L.S.; "Effects of Nutrition and Environment on Brain Biochemistry and Behavior"; Developmental Psychobiology; vol. 16; 1983; pp. 129-145.

Crnic, L.S.; "Maternal Behavior in the Undernourished Rate (Rattus Norvegicus)"; Physiology & Behavior; vol. 16; 1976; pp. 677-680.

Crnic, L.S.; "Models of Infantile Malnutrition in Rats: Effects on Maternal Behavior"; Developmental Psychobiology; vol. 13; 1980; pp. 615-628.

Crnic, L.S.; "Nutrition and Mental Development"; American Journal of Mental Deficiency; vol. 88; No. 5; 1984 pp. 526-533.

Crnic, L.S.; "The Effects of Chronic Lithium Chloride Administration on Complex Schedule Performance, Activity, and Water Intake in the Albino Rat"; Physiological Psychology; vol. 4; 1976; pp. 166-170.

Crnic, L.S.; "The Use of Animal Models to Study Effects of Nutrition on Behavior"; Diet and Behavior: A Multidisciplinary Approach; Springer-Verlag; 1990; pp. 73-87.

Crnic, L.S.; "Transgenic and Null Mutant Animals for Psychosomatic Research"; Psychosomatic Medicine; vol. 58; 1996; pp. 622-632.

Crnic, Linda s. et al., "Automated Analysis of Digitized Videotapes of Mouse Home-Cage Behavior", Feb. 17, 2000.

Dierssen, Mara et al.; "Murine Models for Down Syndrome"; Physiology and Behavior; vol. 73; 2001; pp. 859-871.

Digiscan DMicro System; AccuScan Instruments, Inc., 1996.

Digiscan Model CCDIGI Optical Animal Activity Monitoring System, AccuScan Instruments, Inc., 1997.

Digiscan Optical Animal Activity Monitoring System, AccuScan Instruments, Inc., 1997.

Dorai, C. et al.; "Generating Motion Descriptors From MPEG-2 Compressed HDTV Video for Content-Based Annotation and Retrieval"; In Proceedings of IEEE Third Workshop on Multimedia Signal Processing (MMSP); Sep. 1999; (4pgs).

Dorai, C. et al; "Extracting Motion Annotations From MPEG-2 Compressed Video for HDTV Content Management Applications"; IEEE International Conference on Multimedia Computing and Systems; Jun. 1999; (6pgs).

Dunn, Andrea L. et al.; "Repeated Injections of Interferon-.alpha. A/D in Balb/c Mice: Behavioral Effects"; Brain, Behavior, and Immunity; vol. 7; 1993; pp. 104-111.

EthoVision, computer vision system for automation of behavioral experiments, Noldus Information Technology, 1997.

Fitzgerald, R.E. et al., "Validation of a Photobeam System for Assessment of Motor Activity in Rats," Toxicology, 49 (1988) pp. 433-439.

Granholm, Ann-Charlotte et al.; "Loss of Cholinergic Phenotype in Basal Forebrain Coincides With Cognitive Decline in a Mouse Model of Down's Syndrome"; Experimental Neurology; vol. 161; 2000; pp. 647-663.

Gurney, Mark E. et al. "Motor Neuron Degeneration in Mice That Express a Human Cu,Zn Superoxide Dismutase Mutation" Science 264:1772-1775 (Jun. 17, 1994).

HVS Image Homepage Nov. 25, 1997; Video tracking system for Morris water maze, open field, radial-arm maze, etc.

Hyde, L.A. et al.; "Age-Related Deficits in Context Discrimination Learning in Ts65Dn Mice That Model Down Syndrome and Alzheimer's Disease"; Behavioral Neuroscience; vol. 115; 2001; pp. 1-8.

Hyde, L.A. et al.; "Motor Learning in Ts65Dn Mice, A Model for Down Syndrome"; Developmental Psychobiology; vol. 38; 2001; pp. 33-45.

Hyde, L.A. et al.; "Ts65Dn Mice, A Model for Down Syndrome, Have Deficits in Context Discrimination Learning Suggesting Impaired Hippocampal Function"; Behavioral Brain Research; vol. 118; 2001; pp. 53-60.

Jones, A.P. et al.; "Maternal Mediation of the Effects of Malnutrition"; The Handbook of Behavioral Teratology; Plenum; 1986; pp. 409-425.

Kobla, Vikrant et al.; "Archiving, Indexing, and Retrieval of Video in the Compressed Domain"; In Proceedings of SPIE Conference on Multimedia Storage and Archiving Systems; vol. 2916; Nov. 1996; (12pgs).

Kobla, Vikrant et al.; "Compressed Domain Video Indexing Techniques Using DCT and Motion Vector Information in MPEG Video"; In Proceedings of SPIE Conference on Storage and Retrieval for Image and Video Databases V; vol. 3022; Feb. 1997; (12pgs).

Kobla, Vikrant et al.; "Compressed Domain Video Segmentation"; CFAR Technical Report CS-TR-3688, University of Maryland, College Park; Oct. 25, 1996; (34pgs).

Kobla, Vikrant et al.; "Detection of Slow-Motion Replay Sequences for Identifying Sports Videos"; In Proceedings of IEEE Third Workshop on Multimedia Signal Processing (MMSP); Sep. 1999; (6pgs).

Kobla, Vikrant et al.; "Developing High-Level Representations of Video Clips Using Video Trails"; In Proceedings of SPIE Conference on Storage and Retrieval for Image and Video Databases VI; Jan. 1998; (12pgs).

Kobla, Vikrant et al.; "Extraction of Features for Indexing MPEG-Compressed Video"; In Proceedings of IEEE First Workshop on Multimedia Signal Processing (MMSP); Jun. 1997; (6pgs).

Kobla, Vikrant et al.; "Feature Normalization for Video Indexing and Retrieval"; CFAR Technical Report CS-TR-3732, University of Maryland, College Park; Nov. 1996; (40pgs).

Kobla, Vikrant et al.; "Identifying Sports Videos Using Replay, Text, and Camera Motion Features"; Proceedings of the SPIE Conference on Storage and Retrieval for Media Databases; vol. 3972; Jan. 2000; (12pgs).

Kobla, Vikrant et al.; "Indexing and Retrieval of MPEG Compressed Video"; Journal of Electronic Imaging; vol. 7(2); Apr. 1998; (36pgs).

Kobla, Vikrant et al.; "Special Effect Edit Detection Using Video Trials: A Comparison With Existing Techniquess"; Proceedings of SPIE Conference on Storage and Retrieval for Image and Video Databases VII; Jan. 1999; (12pgs).

Kobla, Vikrant et al.; "Video Trails: Representing and Visualizing Structure in Video Sequences"; In Proceedings of ACM Multimedia Conference; Nov. 1997; (12pgs).

Kram, R., Wong, B. and Full, R.J. 1997. "Three-Dimensional Kinematics and Limb Kinetic Energy of Running Cockroaches". The Journal of Experimental Biology 200, 1919-1929.

Li, Yanbing et al; "Semantic Image Retrieval Through Human Subject Segmentation and Characterization"; In Storage and Retrieval for Image and Video Databases V, SPIE; vol. 3022; 1997; pp. 340-351.

Liang Yiqing et al.; "A Ground Target Detection System for Digital Video Database"; Conference on Visual Information Processing VII, AeroSense '98, Orlando, Florida; Apr. 1998; (6pgs).

Liang, Yiqing et al.; "A Practical Video Indexing and Retrieval System"; Applied Imagery and Pattern Recognition (AIPR) '97, Washington, D.C.; Oct. 1997; (8pgs).

Liang, Yiqing et al.; "Apprenticeship Learning of Domain Models"; Seventh Intl. Conference on Software Engineering and Knowledge Engineering, Rockville, Maryland; Jun. 1995; (9pgs).

Liang, Yiqing et al.; "Multiple Motion Detection Using Genetic Algorithms"; DARPA Image Understanding Workshop, Monterey, CA; Nov. 1998; (8pgs).

Liang, Yiqing et al.; "Toward an Object and Multiple-Modalities Based Indexing and Retrieval of Video Contents"; DARPA's Image Understanding Workshop; Monterey, California; Nov. 1998; (21pgs).

Liang, Yiqing et al; "A Practical Video Database Based on Language and Image Analysis"; AAAI Technical Report, SS-97-03,, ed., Alex Hauptmann & Michael Witbrock, Intelligent Use and Integration of Text, Image, Video and Speech; Mar. 1997; (6pgs).

Liang, Yiqing et al; "A Shot Boundary Detection Algorithm Adapted for Predator Video"; Applied Imagery and Pattern Recognition (AIPR) '98; Washington, D.C.; Oct. 1998; (9pgs).

Liang, Yiqing Ph.D.; "Video Retrieval Based on Language and Image Analysis"; Defense Advanced Research Projects Agency Information Systems Office; May 28, 1999; 35 pgs.

Liang, Yiqing; "A Practical Digital Video Database Based on Language and Image Analysis"; International Conference Multimedia Databases on Internet; Seoul, Korea; Oct. 10, 1997; (23pgs).

Liang, Yiqing, "Digital Video Technologies and Their Applications," Beijing Dec. 2000, 24 pages.

Liu, Bede et al.; "The Princeton Video Library of Politics"; Digital Libraries '94, Texas A & M University; Jun. 1994; pp. 215-216.

Macmillan, D.L. "A Physiological Analysis of Walking in the American Lobster". Feb. 6, 1975. Biological Sciences (England) vol. 270.

Nielsen, D.M. et al.; "Elevated Plus Maze Behavior, Auditory Startle Response,, and Shock Sensitivity in Predisease and in Early Stage Autoimmune Disease MRL/Ipr Mice"; Brain Behavior and Immunity; 2001; pp. 1-16.

Omnitech Electronics, Inc., Olympus 1 Meter .times. 1 Meter Animal Activity Monitor, 1988.

Omnitech Electronics, Inc., Residential Maze Computerized System, 1991.

Ozer, I. Burak et al.; "A Graph Based Object Description for Information Retrieval in Digital Image and Video Libraries"; Proceedings of IEEE Workshop on Content-Based Access of Image & Video Libraries, Colorado; Jun. 1999; (5pgs).

Ozer, I. Burak et al.; "Human Activity Detection in MPEG Sequence"; Proceedings of IEEE Workshop on Human Motion,, Austin; Dec. 2000; pp. 61-66.

Ozer, I. Burak et al., "Human Detection in Compressed Domain." Proceedings of International Conference on Image Processing, Thessaloniki, Greece, Oct. 2001.

Ozer, I. Burak et al.; "Relational Graph Matching for Human Detection and Posture Recognition"; SPIE, Photonic East 2000, Internet Multimedia Management Systems, Boston; Nov. 2000; (12pgs).

Ozer, W. Wolf et al., "Video Analysis for Smart Rooms," Proc. SPIE vol. 4519, p. 84-90, Internet Multimedia Management Systems II, Jul. 2001.

Palmer, James D. et al., "Approaches to Domain Model Construction", Domain Modeling Workshop, 13.sup.th International Conference on Software Engineering, Austin, Texas; Mar. 26, 1991; pp. 130-135.

Palmer, James D. et al.; "Classification As an Approach to Requirements Analysis"; 1.sup.st ASIS SIG/CR Classification Research Workshop, Toronto, Canada; Nov. 4, 1990; pp. 129-136.

Philips, Michael et al.; "A Multi-Attribute Shot Segmentation Algorithm for Video Programs"; Proceedings, SPIE 2916; 1996; (10pgs).

Philips, Michael et al.; "Video Segmentation Techniques for News"; SPIE, vol. 2916; 1996; pp. 243-251.

RotoScan, Rotometer High Resolution Rotation Monitoring; AccuScan Instruments, Inc., 1993.

Sago, Haruhiko et al.; "Genetic Dissection of Region Associated With Behavioral Abnormalities in Mouse Models for Down Syndrome"; Pediatric Research; vol. 48; No. 5; 2000; pp. 606-613.

Sakic, Boris et al.; "Reduced Corticotropin-Releasing Factor and Enhanced Vasopressin Gene Expression in Brains of Mice With Autoimmunity-Induced Behavioral Dysfunction"; Journal of Neuroimmunology 96; 1999; pp. 80-91.

San Diego Instruments Behavioral Testing Systems, Nov. 19, 1997 (18 pages).

Schrott, Lisa M. et al., "Sensitivity to Foot Shock in Autoimmune NZB .times. NZW F1 Hybrid Mice"; Physiology & Behavior; vol. 56; No. 5; 1994; pp. 849-853.

Schrott, Lisa M. et al.; "Anxiety Behavior, Exploratory Behavior, and Activity in NZB .times. NZW F1 Hybrid Mice: Role of Genotype and Autoimmune Disease Progression"; Brain, Behavior and Immunity; vol. 10; 1996; pp. 260-274.

Schrott, Lisa M. et al.; "Increased Anxiety Behaviors in Autoimmune Mice"; Behavioral Neuoscience; vol. 110; No. 3; 1996; pp. 492-502.

Schrott, Lisa M. et al.; "The Role of Performance Factors in the Active Avoidance-Conditioning Deficit in Autoimmune Mice"; Behavioral Neuroscience; vol. 110; No. 3; 1996; pp. 486-491.

Schrott,, Lisa M. et al.; "Attenuation of Behavioral Abnormalities in Autoimmune Mice by Chronic Soluble Interferon-.gamma. Receptor Treatment"; Brain, Behavior and Immunity; vol. 12; 1998; pp. 90-106.

Segall, M.A. et al.; "A Test of Conditioned Taste Aversion With Mouse Interferon-.alpha."; Brain, Behavior and Immunity; vol. 4; 1990; pp. 223-231.

Segall, M.A. et al.; "An Animal Model for the Behavioral Effects of Interferon"; Behavioral Neuroscience; vol. 104; No. 4; 1990; pp. 612-618.

The Observer, Professional system for collection, analysis and management of observational data, Noldus Information Technology, 1996.

Tremorscan Monitor Model TS1001; AccuScan Instruments, Inc., 1997.

Wolf, W.; "Key Frame Selection by Motion Analysis"; Proceedings, ICASSP, IEEE Press; 1996; (4pgs).

Wolf, Wayne et al.; "A Digital Video Library for Classroom Use"; International Conference on Digital Library '95, Tsukuba; Aug. 1995; (6pgs).

Wolf, Wayne et al.; "A Digital Video Library on the World Wide Web"; ACM Multimedia '96, Addison-Wesley, Publishing Company; Nov. 1996; pp. 433-434.

Wolf, Wayne et al., "A Smart Camera for Real-Time Human Activity Recognition," 2001 IEEE Workshop on Signal Processing Systems, Antwerp, Belgium, Sep. 2001.

Wolf, Wayne; "Hidden Markov Model Parsing of Video Programs"; IEEE; 1997; pp. 2609-2611.

Yeo, B.L. et al.; "Theft-Resistant Video Browsing Using Filtered Versions of Compressed Sequences"; IEEE Conference on Multimedia Computing and Systems; 1995; (6pgs).

Yeung, Minerva M. et al.; "Video Browsing Using Clustering and Scene Transitions on Compressed Sequences"; SPIE Conference on Multimedia Computing and Networking; vol. 2417, 1995; pp. 399-413.

Yu, H. et al.; "A Visual Search System for Video and Image Databases"; IEEE Multimedia; 1997; (8pgs).

Yu, H. et al.; "Hierarchical, Multi-Resolution Algorithms for Dictionary-Driven Content-Based Image Retrieval"; International Conference on Image Processing; 1997; (4pgs).

Yu, H. et al.; "Scenic Classification Methods for Image and Video Databases"; SPIE; vol. 2606; 1995; pp. 363-371.

Yu, Hong-Heather et al.; "A Hierarchical Multiresolution Video Shot Transition Detection Scheme"; Computer Vision and Image Understanding; vol. 75; Jul./Aug. 1999; pp. 196-213.

Yu, Hong-Heather et al.; "Multi-Resolution Video Segmentation Using Wavelet Transformation"; In Storage and Retrieval for Image and Video Databases VI, SPIE; vol. 3312; 1998; pp. 176-187.

Yu, Hong-Heather et al; "A Multi-Resolution Video Segmentation Scheme for Wipe Transition Identification"; In Proceedings IEEE ICASSP; vol. 5; 1998; pp. 2965-2968.

Yu, Hong-Heather et al; "A Visual Search System for Video and Image Databases"; In Proceedings, ICMCS 1997, IEEE Computer Society Press; 1997; pp. 517-524.

Zeng, H. et al; "Data Mining for Combat Vehicle Classification Using Machine Learning"; Applied Imagery and Pattern Recognition (AIPR) '98, Washington, D.C.; Oct. 1998; (10pgs).

\* cited by examiner

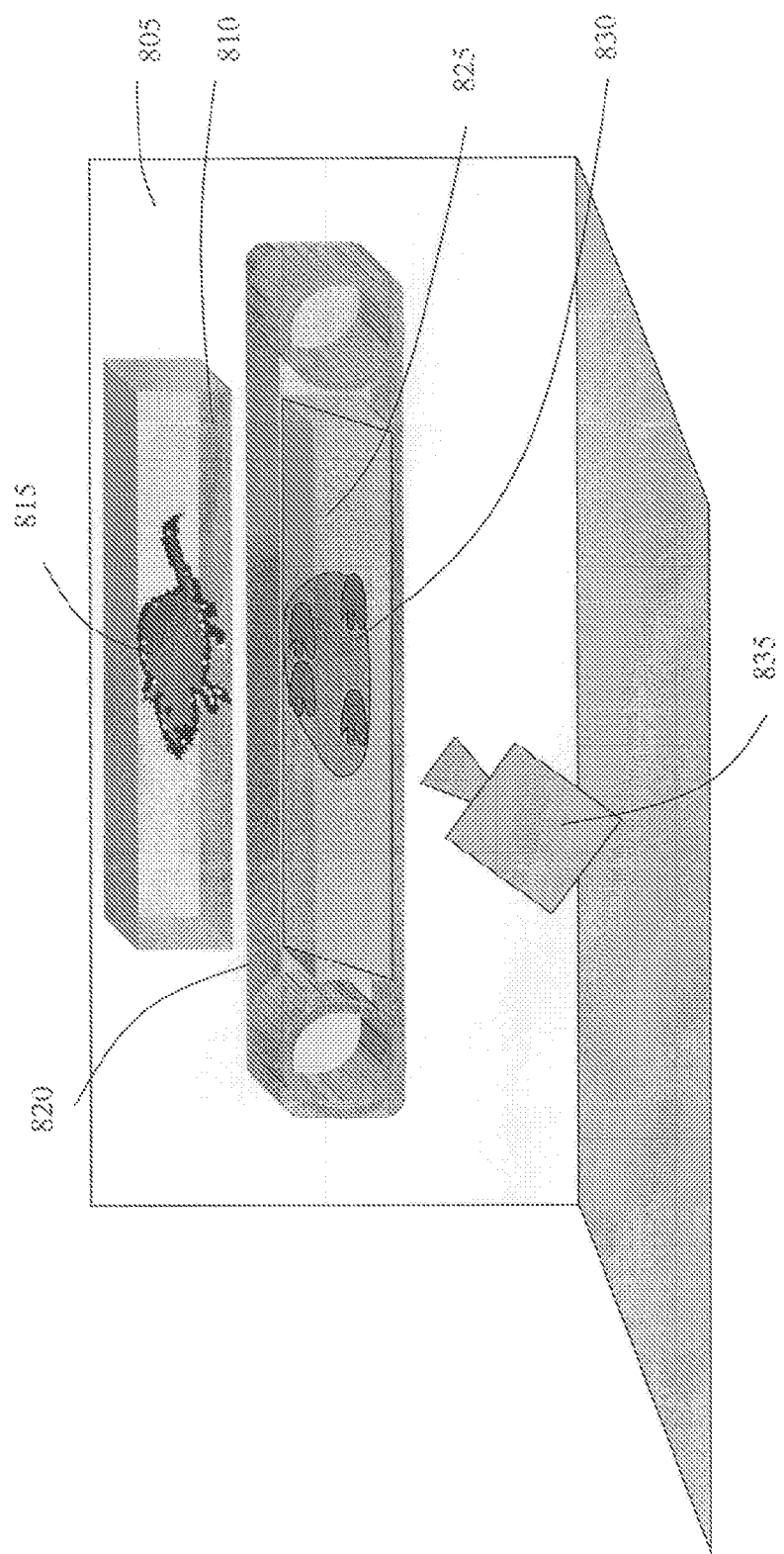

SYSTEM AND METHOD FOR ANIMAL GAIT CHARACTERIZATION FROM BOTTOM VIEW USING VIDEO ANALYSIS

CROSS-REFERENCE TO RELATED APPLICATIONS

This application is a continuation-in-part of U.S. patent application Ser. No. 09/718,374, filed Nov. 24, 2000, now issued as U.S. Pat. No. 6,678,413.

BACKGROUND OF THE INVENTION

1. Technical Field

The invention relates generally to gait analysis of animal objects. More particularly, one aspect of the invention is directed to monitoring and characterization of walking and running behaviors under a controlled environment for an animal, for example, a mouse or a rat, using video analysis from a bottom view image, either obtained directly by placing a camera underneath a transparent treaded treadmill or by placing a mirror that reflects the bottom view image onto the side where the camera can capture them. In all cases, a treadmill with a transparent tread or belt is used.

2. Background Art

Animals, for example mice or rats, are used extensively as human models in the research of drug development; genetic functions; toxicology research; understanding and treatment of diseases; and other research applications. Despite the differing lifestyles of humans and animals, for example mice, their extensive genetic and neuroanatomical homologies give rise to a wide variety of behavioral processes that are widely conserved between species. Exploration of these shared brain functions will shed light on fundamental elements of human behavioral regulation. Therefore, many behavioral test experiments have been designed on animals like mice and rats to explore their behaviors. These experiments include, but not limited to, home cage behaviors, open field locomotion experiments, object recognition experiments, a variety of maze experiments, water maze experiments, freezing experiments for conditioned fear, and gait analysis experiments. All these apparatus and experiments use, in many cases, human observation of videotapes of the experiment sessions, resulting in inaccuracy, subjectivity, labor-intensive, and thus expensive experiments.

Of particular interest here are the gait analysis experiments. The purpose of the gait analysis experiments is to enable the scientist to measure various parameters of walking or running behaviors including, but not limited to, stride length, stride speed, time of contact of feet with the floor, spacings between feet, trajectories of the individual feet, etc.

Scientists have two available methods to generate these strides from an animal—1) placing the animal on an art paper with its feet dipped in ink and letting the animal walk on the paper thereby generating footprints in the paper and measuring parameters from these footprints; and 2) placing the animal on a treadmill and manually observing the video and scoring the parameters from the video data. Usually, this treadmill is a conventional animal treadmill with an opaque belt. Hence, the parameter measurements are extremely difficult to determine accurately. In the first case, the footprints are never accurate as artifacts such as blotches, ink drops, or irregular prints can generate unreliable results. In both of these cases, the manual measurement process is a slow, tedious, and highly-subjective process.

Instead of using an opaque belt for the treadmill approach, a transparent belt can be used and the walking animal can be observed through this transparent belt. This introduces the opportunity to utilize the latest technologies in computer vision, image processing, and digital video processing to automate the processes and achieve better results, high throughput screening, and lower costs.

SUMMARY OF THE INVENTION

There are strong needs for automated systems and software that can automate the measurements of the experiments mentioned above, provide the measurements of meaningful complex behaviors and revealing new parameters that characterize animal behaviors to meet post-genomic era's demands, and obtain consistent results using novel approaches.

A revolutionary approach is invented to automatically measure animal's gait patterns. This approach consists of capturing video from underneath with the animal walking on a treadmill with a transparent tread (or belt) and analyzing the motion patterns of its feet. Computer systems are integrated with a high-speed camera capture system and implemented that can produce digital video files of animal's gait patterns in a real time or off-line mode. Software algorithms are developed to automatically calculate the various gait parameters from those video files.

Creative algorithms are designed to extract images of the feet from the rest of the body of animals such as mice or rats. This analysis is based on the premise that the entire animal body, body parts including feet, related color information, and their dynamic motion are taken advantage of in order to provide the measurement of the various parameters.

Virtual apparatus is designed and implemented in the system to ensure same software framework can be applied to different types of treadmills, and animal object of any color and shape, instead of having different software components to handle different apparatuses. The software is designed to provide graphic tools, and users can use these graphic tools to create virtual apparatus corresponding to the real apparatus that is being used for the experiment under observation. Graphic tools also provide the capability to calibrate these apparatus, allowing better identification of the body and its body parts, and precise measurement of gait parameters in real measurements instead of relative measurement using number of pixels.

In general, the present invention is directed to systems and methods for finding patterns and parameters of gait behavior of an animal using video. The invention includes a system with a high-speed video camera connected to a computer in which the computer is configured to automatically provide animal identification, body part identification, especially the feet, motion tracking (for moving feet), and parameter calculation. Thus, the present invention is capable of automatically monitoring a sequence of video images to identify, track and classify the gait behavior of various animals. The video image may be provided in real time from a camera and/or from a storage location. The invention is particularly useful for monitoring and measuring parameters of gait behavior of mice or rats for testing impairments caused by neurological diseases, drugs, or genetic mutations, but may be used in any of a number of surveillance or other applications.

In one embodiment the invention includes a system in which an analog/digital high-speed video camera is coupled to a video digitization/compression unit. The video camera may provide a video image containing an animal to be identified. The video digitization/compression unit is coupled to a computer that is configured to automatically monitor the video image to identify, track and classify the actions of the animal and its movements over time within a sequence of video session image frames. The digitization/compression unit may convert analog video and audio into, for example, MPEG or other formats. The computer may be, for example, a personal computer, using either a Windows platform or a Unix platform, or a MacIntosh computer and compatible platform. The computer is loaded and configured with custom software programs (or equipped with firmware) using, for example, MATLAB or C/C++ programming language, so as to analyze the digitized video for animal identification and segmentation, tracking, and/or behavior/activity characterization. This software may be stored in, for example, a program memory, which may include ROM, RAM, CD ROM and/or a hard drive, etc.

In operation, the system receives incoming video images from either the video camera in real time or pre-recorded from the video record/playback unit. If the video is in analog format, then the information is converted from analog to digital format and may be compressed by the video digitization/compression unit. The digital video images are then provided to the computer where various processes are undertaken to identify and segment a predetermined animal from the image. In a preferred embodiment the animal is a mouse or rat in motion with some movement from frame to frame in the video, and is in the foreground of the video images. In any case, the digital images may be processed to identify and segregate a desired (predetermined) animal from the various frames of incoming video. This process may be achieved using, for example, background subtraction, mixture modeling, robust estimation, and/or other processes.

The shape and location of the desired animal is then tracked from one frame or scene to another frame or scene of video images. The body parts of the animal such as head and tail are identified by novel approaches through shape analysis. Next, the individual feet are identified and assigned appropriate labels such as Front-Right-Foot, Front-Left-Foot, Rear-Right-Foot, and Rear-Left-Foot by using the head and tail and orientation parameters. Once the feet are identified, they are tracked using data propagation from one frame to frame (correspondence calculation), and relative positioning information when such frame-to-frame correspondence calculation is not sufficient such as the left foot will always be to the left of the right foot, and the front foot will always be closer to the head than the rear foot, etc. The patterns of movements of these individual feet are then analyzed and their motion parameters such as stride length, spacing between feet, etc. are calculated.

In another preferred embodiment directed toward the video camera providing a video image containing animals such as mice or rats to be analyzed, there are at least one camera or multiple cameras taking video image of experiment apparatus that contain animals. There is at least one apparatus, or as many as the computer computing power allows, say four (4) or sixteen (16) or even more. Each apparatus contains at least one animal or multiple animals. The multiple cameras may be taking video from different points of views such as one taking bottom-view video images from underneath the apparatus, or one taking video images from the side of the apparatus. These apparatus can be treadmills or other types of animal motion generation devices. When video images are taken of multiple apparatuses and devices containing one or multiple animals, and are analyzed for identifying these animals' behaviors, high throughput screening is achieved. When video images taken from different points of views, for example, one from the bottom view and another from the side view, are combined to identify animal's behaviors, integrated analysis is achieved.

Development activities have been completed to validate various scientific definitions of gait behaviors and to create novel digital video processing algorithms for feet tracking and gait analysis, which are embodied in a software and hardware system according to the present invention.

Thus, the automated analysis of the present invention may be used to build profiles of the gait parameters such as their amount, duration, and other salient parameters for each animal, for example each commonly used strain of mice. A plurality of such profiles may be stored in, for example, a database in a data memory of the computer. One or more of these profiles may then be compared to a mouse in question and difference from the profile expressed quantitatively.

The techniques developed with the present invention for automation of the categorization and quantification of gait behaviors is a powerful tool for detecting neurological abnormalities in mice. These parameters provide good indications for gene targeting, drug screening, toxicology research, understanding and treatment of diseases such as Parkinson's Disease, Alzheimer Disease, ALS, etc. As previously discussed, this technology is extendable to other behavior studies of animals and humans, as well as surveillance purposes. As will be described in detail below, the present invention provides automated systems and methods for automated accurate identification, tracking and behavior categorization of the feet of an object whose image is captured with video.

BRIEF DESCRIPTION OF THE DRAWINGS

FIG. 8 shows one exemplary apparatus—a treadmill with a tilted mirror that is used to capture the bottom-view gait images with the foot patterns. The feet with distinct color are shown.

DESCRIPTION OF THE PREFERRED EMBODIMENTS

Figure 1:
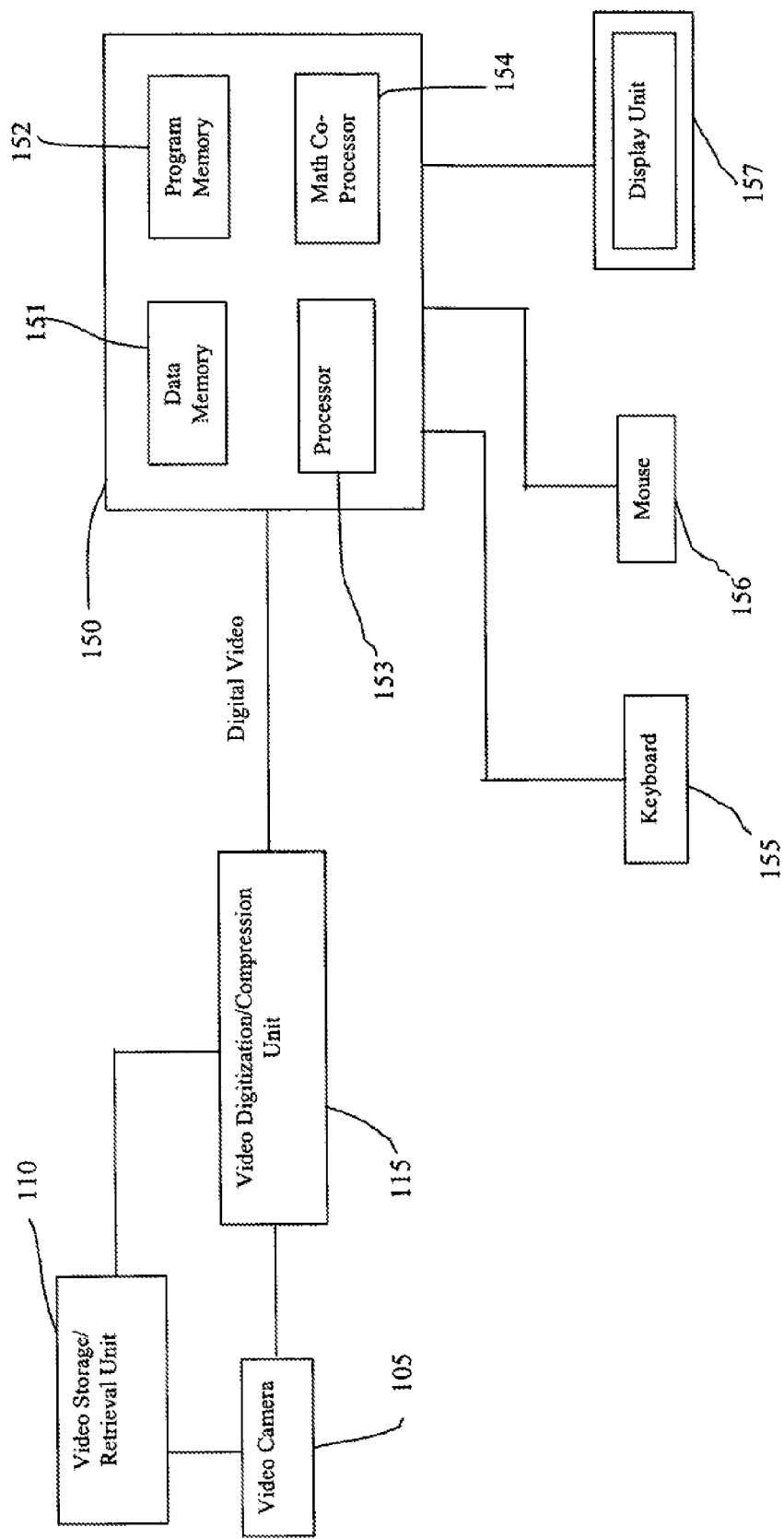
FIG. 1 is a block diagram of one exemplary system configurable to find the position, shape, and behavioral characteristics of an object using automated video analysis, according to one embodiment of the present invention.

The past few years has seen an increase in the integration of video camera and computer technologies. Today, the integration of the two technologies allows video images to be digitized, stored, and viewed on small inexpensive computers, for example, a personal computer. Further, the processing and storage capabilities of these small inexpensive computers has expanded rapidly and reduced the cost for performing data and computational intensive applications. Thus, video analysis systems may now be configured to provide robust tracking systems that can provide automated analysis and identification of various objects and characterization of their behavior. The present invention provides such systems and related methods.

In general, the present invention can automatically find the patterns of gait behaviors and/or activities of a predetermined object being monitored using video. The invention includes a system with a video camera connected to a computer in which the computer is configured to automatically provide object identification, foot identification and segregation, foot tracking, and gait parameter calculation based on the trajectories of the individual feet. In a preferred embodiment the system includes various video analysis algorithms. The computer processes analyze digitized video with the various algorithms so as to automatically monitor a video image to identify, track and classify the walking or running behaviors of one or more predetermined objects captured by the video image as it occurs from one video frame or scene to another. The system may characterize gait behavior by calculating a set of gait parameters from the tracked feet data. The image to be analyzed may be provided in real time from one or more cameras and/or from storage.

In various exemplary embodiments described in detail as follows, the invention is configured to enable monitoring gait behaviors of rodents and other animals such as walking and running behavior patterns including speed, length of strides, spacing between feet and synchronization parameters between feet. The system may also be configured to automatically identify and characterize human gait behavior for tasks such as neurodegenerative diseases, rehabilitation analysis, etc. However, as indicated above, the system may be similarly configured for use in any of a number of surveillance or other applications. For example, the invention can be applied to various situations in which tracking moving objects is needed. The invention may be capable of identifying and understanding subtle behaviors involving portions of body such as forelimb and can be applied to identify and understand human gesture recognition. This could help deaf individuals communicate. The invention may also be the basis for computer understanding of human gesture to enhance the present human-computer interface experience, where gestures will be used to interface with computers. The economic potential of applications in computer-human interface applications and in surveillance and monitoring applications is enormous.

In one preferred embodiment illustrated in FIG. 1, the invention includes a system in which an analog video camera 105 and a video storage/retrieval unit 110 may be coupled to each other and to a video digitization/compression unit 115. The video camera 105 may provide a real time video image containing an object to be identified. The video storage/retrieval unit 110 may be, for example, a VCR, DVD, CD or hard disk unit. The video digitization/compression unit 115 is coupled to a computer 150 that is configured to automatically monitor a video image to identify the animal, segregate the feet, track the feet and calculate the gait parameters of the object within a sequence of images. The digitization/compression unit 115 may convert analog video and audio into, for example, MPEG format, Real Player format, etc. The computer may be, for example, a personal computer, using either a Windows platform or a Unix platform, or a MacIntosh computer and compatible platform. In one variation the computer may include a number of components such as (1) a data memory 151, for example, a hard drive or other type of volatile or non-volatile memory; (2) a program memory 152, for example, RAM, ROM, EEPROM, etc. that may be volatile or non-volatile memory; (3) a processor 153, for example, a microprocessor; and (4) a second processor to manage the computation intensive features of the system, for example, a math co-processor 154. The computer may also include a video processor such as an MPEG encoder/decoder. Although the computer 150 has been shown in FIG. 1 to include two memories (data memory 151 and program memory 152) and two processors (processor 153 and math co-processor 154), in one variation the computer may include only a single processor and single memory device or more then two processors and more than two memory devices. Further, the computer 150 may be equipped with user interface components such as a keyboard 155, electronic mouse 156, and display unit 157.

In one variation, the system may be simplified by using all digital components such as a digital video camera and a digital video storage/retrieval unit 110, which may be one integral unit. In this case, the video digitization/compression unit 115 may not be needed.

The computer is loaded and configured with custom software program(s) (or equipped with firmware) using, for example, MATLAB or C/C++ programming language, so as to analyze the digitized video for object identification and segmentation, tracking, and/or behavior/activity characterization. This software may be stored in, for example, a program memory 152 or data memory that may include ROM, RAM, CD ROM and/or a hard drive, etc. In any case, the algorithms may be implemented in software and may be understood as unique functional modules as shown in FIG. 2 and now described.

Figure 2:
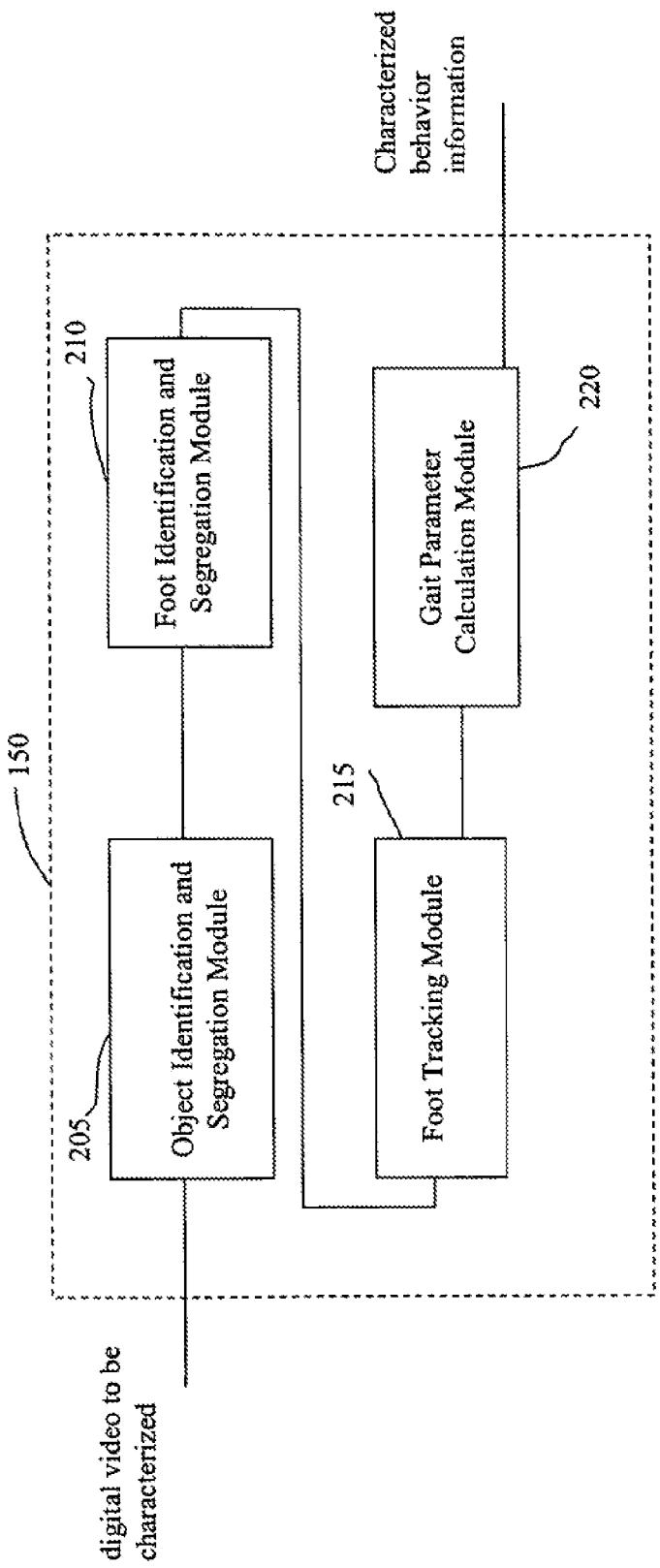
FIG. 2 is a block diagram of various functional portions of a computer system, such as the computer system shown in FIG. 1, when configured to find the position, shape, and gait parameters of the feet of an object using automated video analysis, according to one embodiment of the present invention.

Referring to FIG. 2, in the automatic gait analysis process, digital video (either real-time and/or stored) of objects to be analyzed for gait behavior is input to an object identification and segregation module 205. This module identifies and segregates a predetermined type of object from the digital video image and inputs it to a foot identification and segregation module 210. The foot identification and segregation module 210 extracts the feet from the rest of the body of the animal. These extracted feet objects only are input to the foot tracking module 215. This module generates and maintains the position history of the feet from which the gait parameters are calculated. This position history and other tracked information is passed onto the Gait Parameter Calculation Module 220 for calculating all the requisite gait parameters. This information is output to the user as characterized behavior information on, for example, a display unit 157.

Figure 3:
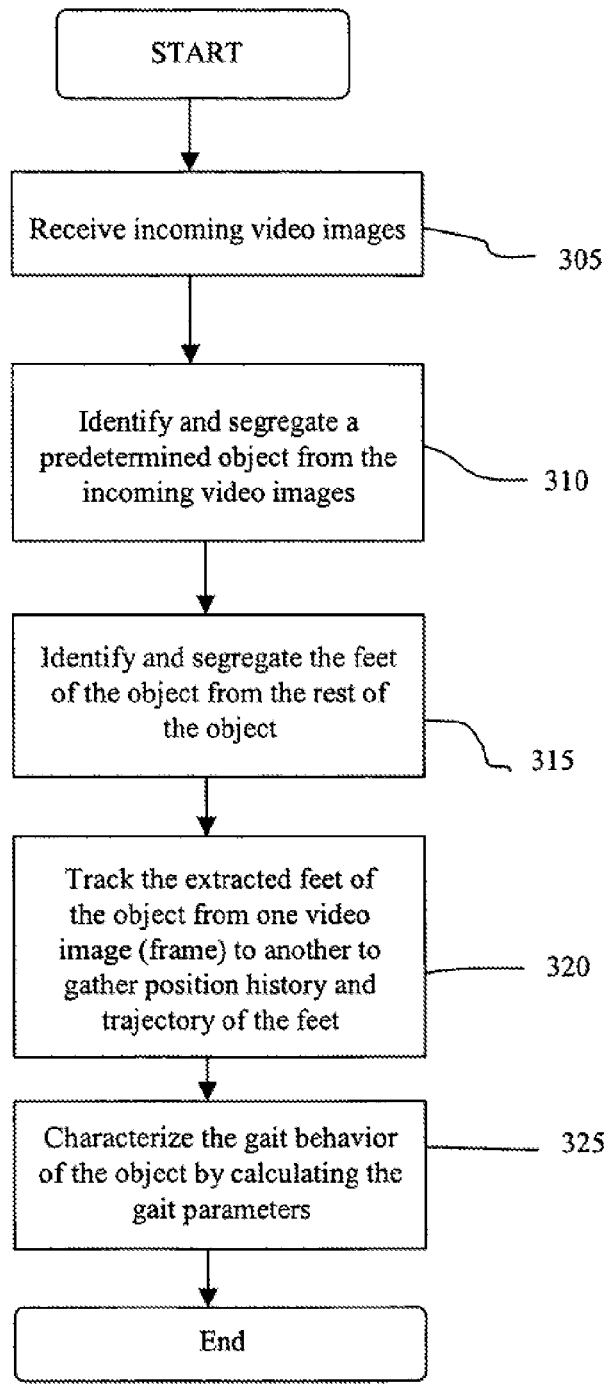
FIG. 3 is a flow chart of a method of automatic video analysis for gait behavior characterization, according to one embodiment of the present invention.

Referring now to FIG. 3, a general method of operation for one embodiment of the invention will be described. In operation, in the video analysis mode the system may receive incoming video images at step 305, from the video camera 105 in real time, pre-recorded from the video storage/retrieval unit 110, and/or a memory integral to the computer 150. If the video is in analog format, then the information is converted from analog to digital format and may be compressed by the video digitization/compression unit 115. The digital video images are then provided to the computer 150 for various computational intensive processing to identify and segment a predetermined object from the image. In a preferred embodiment, the object to be identified and whose gait behaviors are to be characterized is a moving object, for example a mouse, which has some movement from frame to frame or scene to scene in the video images and is generally in the foreground of the video images. In any case, at step 310 the digital images may be processed to identify and segregate a desired (predetermined) object from the various frames of incoming video. This process may be achieved using, for example, background subtraction, mixture modeling, robust estimation, and/or other processes.

Next, at step 315, the segregated object may be processed to identify and segregate its feet. As will be discussed in more detail below, this identification and segregation may be achieved by, for example, generating a color model for each of the individual feet. Next, at step 320, the changes in the features of the feet of the object, such as the shapes, locations, and sizes of the feet of the object of interest, may be identified. Then, at step 325, the states of the object, for example the shape, location, and size, may be used to calculate the gait parameters of the object.

Types of parameters that may also be calculated include stride lengths and times, stance and swing times, running speeds, foot spacing parameters, and coupling parameters. From these calculations, the system may be capable of characterizing the gait behavior.

Figure 4:
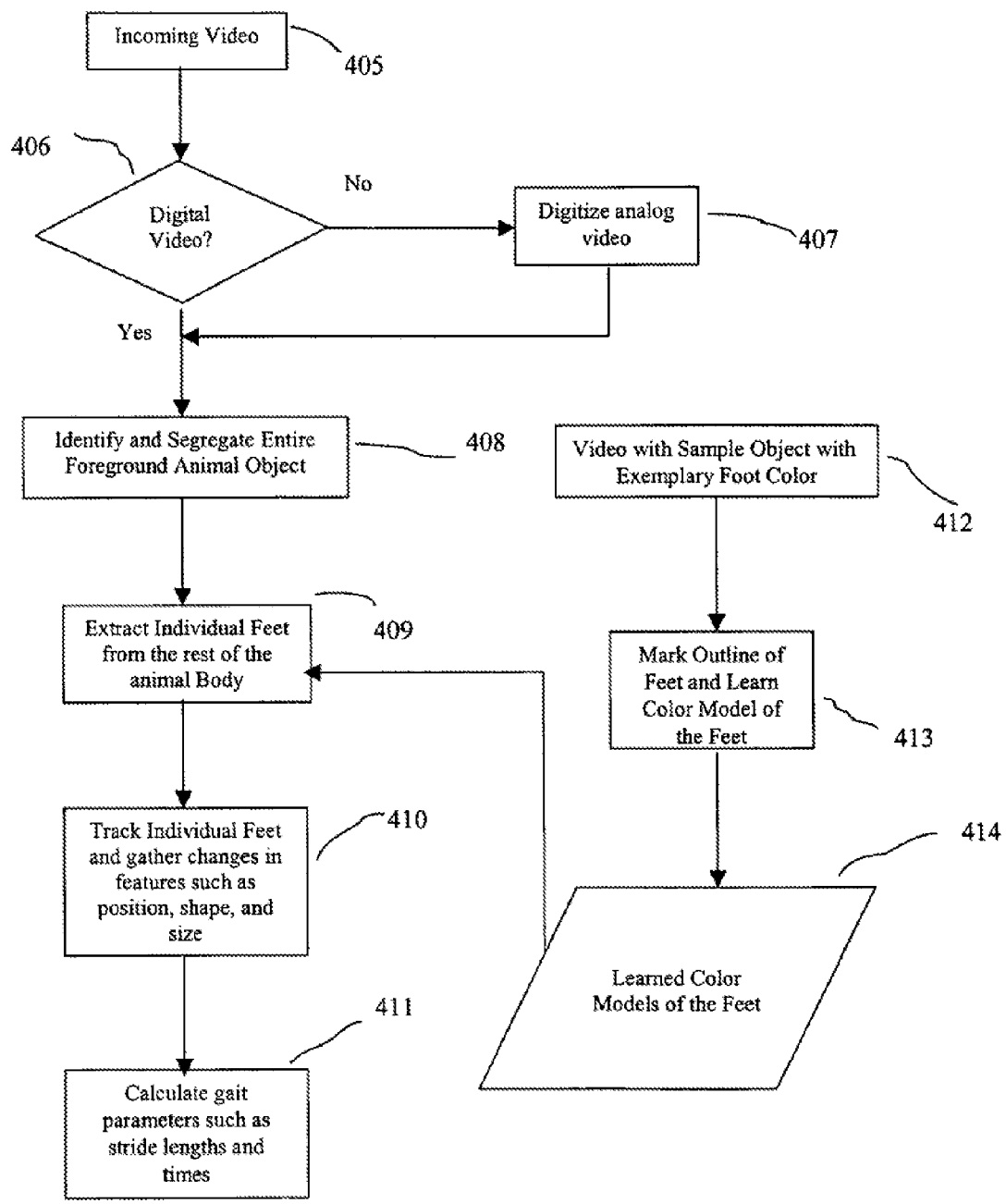
FIG. 4 is a flow chart of a method of automatic video analysis for gait behavior characterization, according to another embodiment of the present invention.

Referring now to FIG. 4 a more detailed description of another preferred embodiment will be described. In this case the system is directed toward video analysis of animated objects such as a mouse or a rat. As a preliminary matter, at step 412 video of the activities of a sample object are input into the system. This information may be provided from a video storage/retrieval unit 110 in digitized video form. This information may then be manually categorized at step 413 by outlining the individual feet by a user viewing the video images on the display unit 157. The system may then learn the color models of the outlined feet and store these color models in memory at step 414. This information provides a point of reference for video analysis to identify the feet in new video.

Once information related to identifying the feet of an object is established, the system may then be used to analyze incoming video images that may contain an object and its feet for which automated gait behavior characterization is desired. First, at step 405, incoming video images are received. Next, at decision step 406, the system determines if the video images are in analog or digital format. If the video images are in analog format they are then digitized at step 407. The video may be digitized and may be compressed, using, for example, a digitizer/compression unit 115 into a convenient digital video format such as MPEG, RealPlayer, etc. Otherwise, the digital video image may be input directly to the computer 150. Now the object of interest is identified within the video images and segregated for analysis. As such, at step 408, a foreground object may be detected. For example, a mouse on a transparent treadmill is detected in the foreground and segregated from the background. Then, at step 409, using the color models stored in 414, the individual feet of the foreground object are identified and segregated.

Then, at step 410, the extracted feet at each frame is tested with the current tracks of all the feet. Correspondences are generated and the detected feet in the current video frame are assigned to the appropriate tracks. Thus, tracking is achieved and the position, shape and size history of each of the feet is updated.

At steps 411, various gait parameters from the position, shape and size history of the individual feet are calculated and output. In one variation of the invention, the information output may include information that is compatible with current statistical packages such as Systat and SPSS, or spreadsheet applications such as Microsoft Excel.

The present invention is designed particularly for the purpose of automatically determining the gait behavioral characteristics of a mouse or a rat. Measurement and analysis of gait has been successfully applied to every common laboratory species and many others as well. It has provided a detailed basic understanding of human and quadruped locomotion and is a now a common cross-species clinical tool that is sensitive to relatively minor changes associated with disease, injury or rehabilitation. In its most sophisticated form, analysis of gait can include synchronized collection of ground reaction forces, kinematic and electromyographic data. The difficulty of scaling and applying these techniques to mice has limited its use despite a steady increase in the use of mice for study of motor system diseases.

A simple but related method that has been successfully used in mice is "foot painting." This requires application of ink to the animal's feet and then measurement of static gait parameters (e.g. stride length) from the resulting footprints. This approach is simple and reasonably sensitive but has significant practical limitations. The present invention has extended this simple approach by using digital video capture of foot placements of nice during treadmill locomotion and then generating standard gait measures from the video images, all in an automated process.

Videos are taken in a standard laboratory environment using commercially available high-speed cameras 105 to ensure that the speed of the foot movements can be captured with an acceptable temporal resolution.

Referring again to FIG. 3, the first step in the gait analysis is an automated initialization step that involves analysis of video images to identify the location and outline of the entire mouse or rat body, as indicated by step 310. Second, the extracted animal body is analyzed thoroughly and all body parts within this entire body that matches the color model of the feet (pre-trained models are generated by the user using foot samples) are identified and segregated, as indicated by step 315. Performing the initialization step periodically, even at every frame, may be used to reset any propagation errors that appear during the foot tracking step. As the feet of the animal are detected in every frame over time, correspondence matching is performed next to assign the detected feet at every frame with the continuing tracks of the feet from history. This tracking procedure enables each foot to be tracked independently of the other feet, and a complete history of each foot with all features such as position, shape, and size are maintained, as indicated by step 320. From this history of the individual foot features, various parameters descriptive of the gait of the animal are calculated, as indicated by step 325. Detailed descriptions of these steps are now presented.

I. Animal Body Detection and Outline Identification

The first step in analyzing the gait behavior of the animal is to locate and extract the entire animal itself. A pre-generated background of the video clip in question is first obtained and it is used to determine the foreground objects by taking the intensity difference and applying a threshold procedure to remove noise. This step may involve threshold procedures on both the intensity and the size of region. An 8-connection labeling procedure may be performed to screen out disconnected small noisy regions and improve the region that corresponds to the mouse. In the labeling process, all pixels in a frame will be assigned a label as foreground pixel or background pixel based on the threshold. The foreground pixels are further cleaned up by removing smaller components and leaving only the largest component as the foreground object. Those foreground pixels that border a background pixel form the contour for the object. The outline or contour of this foreground object is thus determined. The centroid (or center of mass) of the foreground object is calculated and is used for representing the location of the object (e.g., mouse).

Figure 5A:
FIG. 5A illustrates a sample video image frame with a mouse in a treadmill with a transparent tread and captured from the side with a tilted mirror placed underneath the transparent tread that reflects the bottom-view image to the side and is captured by a high-speed camera placed on the side of the treadmill.
Figure 5B:
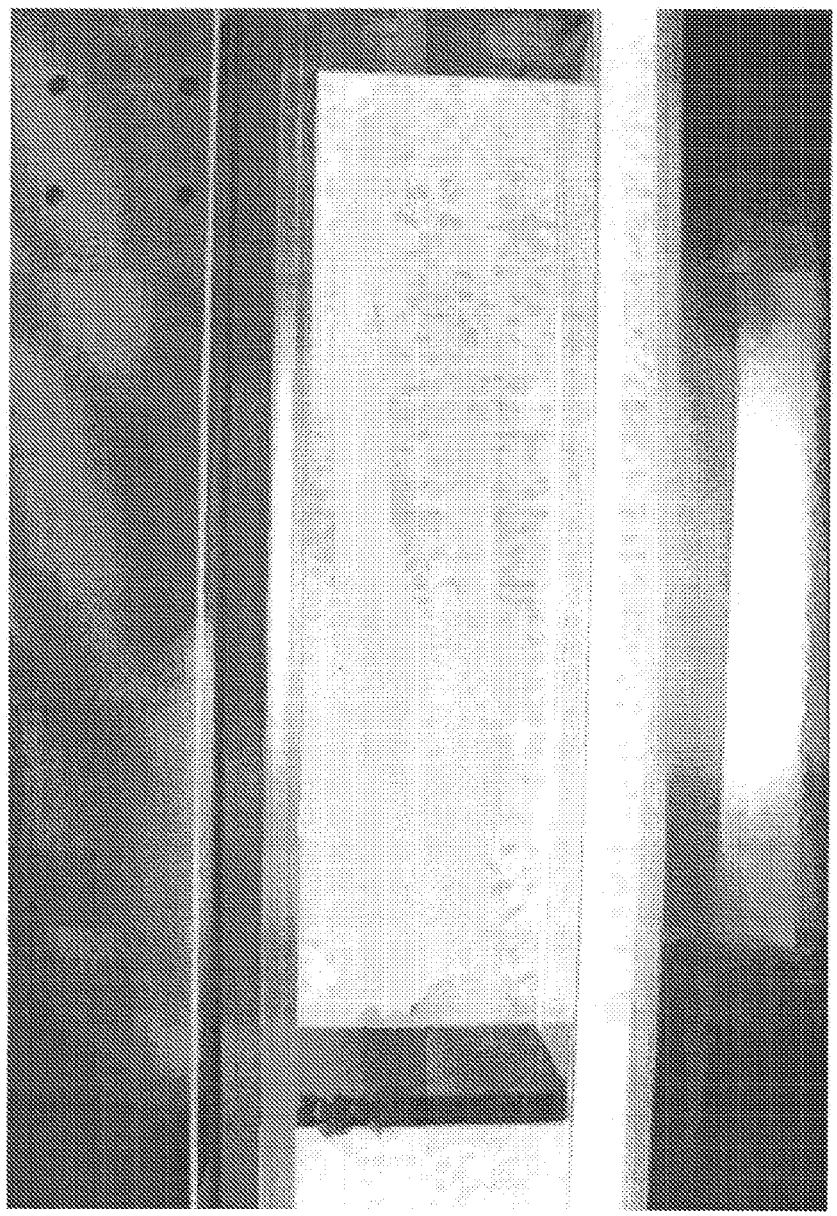
FIG. 5B shows the background image of the same setup without the animal placed in the cage.
Figure 6A:
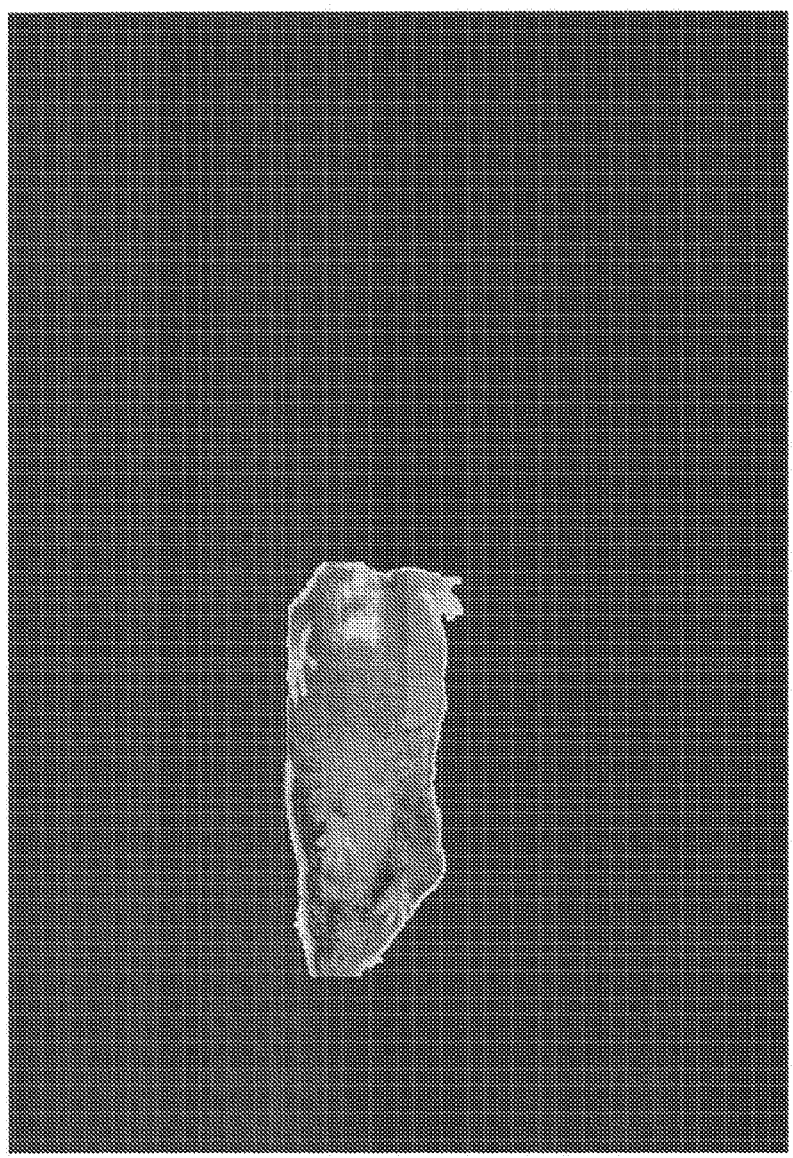
FIG. 6A illustrates the extracted foreground object from the rest of the background. Only the mouse object is detected.
Figure 6B:
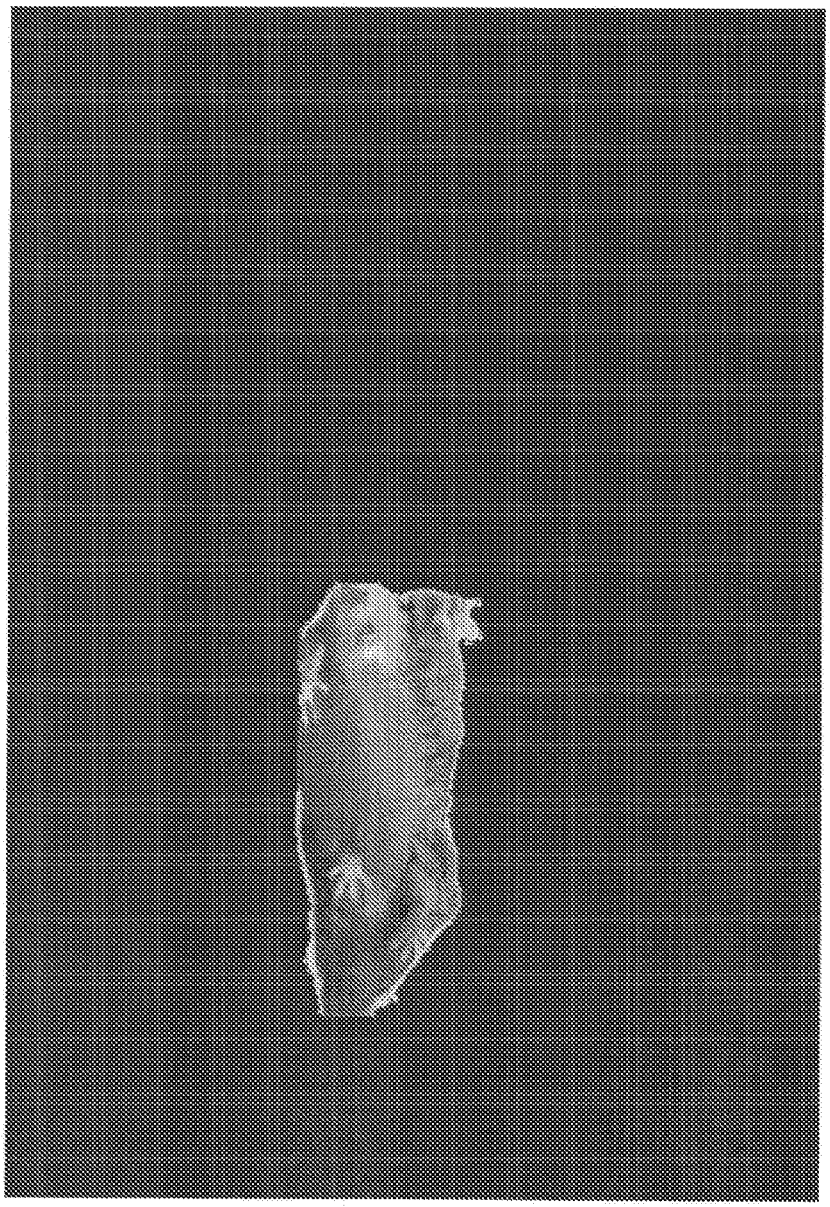
FIG. 6B shows the same figure, but with the outline of the detected foreground object.

FIGS. 5A, 5B, 6A, and 6B illustrate the results of the location and object outline identification for a mouse using the present invention. FIG. 5A shows the original image, and FIG. 5B shows a background image for this setup. Note that it does not contain the animal but, otherwise is almost identical to the FIG. 5A. FIG. 6A illustrates the detected foreground image of the original image from FIG. 5A, and FIG. 6B shows the same extracted full body, except this one contains an outline or contour.

The contour representation, apart from other features that include but not limited to: centroid, the principal orientation angle of the object, the area (number of pixels), the eccentricity (roundness), and the aspect ratio of object, can be used as features of the foreground object to detect its orientation and also can be used to detect the body parts such as head/mouth, tail and the feet. Detecting the proper orientation of the full animal enables the proper detection of the feet, as predictive zones for each of the feet can now be localized better. Also, once the feet are detected, appropriate assignments such as which one is front-left, which one is rear-right etc., can be done correctly.

II. Foot Identification and Segregation

Once the full foreground object body of the animal is detected, the next step is to detect the feet from the bottom-view image. The feet of the animal have a distinct color from the rest of the body when they are in contact with the transparent tread. This feature is exploited by this invention and color models for the feet are pre-trained by the user demarcating the foot areas in the training video frames.

Once the foot models have been teamed, these models can be used to identify the feet in the videos to be analyzed. For each of the feet, two color distribution models are learned: Absolute RGB, and Normalized RGB distributions. During the training phase, regions demarcated by the user as representing a particular foot are analyzed and all the pixels within the region are accumulated in a color histogram distribution. In the Absolute RGB histogram, the respective histogram bins representing the R, G, and B values ranging from 0 to 255, are incremented. In the Normalized RGB histogram, the values representing R/(R+G+B), B/(R+G+B), and G/(R+G+B) are calculated normalized between 0 and 255, and these normalized values are used to generate the histogram distributions.

Armed with these Absolute RGB and Normalized RGB distributions as foot color models, all pixels in the detected foreground object are tested to see if they fit these histogram distributions correctly. If so, they are detected as foot pixels.

Once all the foot pixels have been selected, neighboring 8-connected pixels are grouped together to form larger foot regions, similar to the earlier step for detecting the entire foreground body. Small foot regions are discarded and the remaining foot candidates are tested for correspondences with detected foot regions in the previous video frame.

Figure 7A:
FIG. 7A depicts another sample video image frame, similar to FIG. 5A.
Figure 7B:
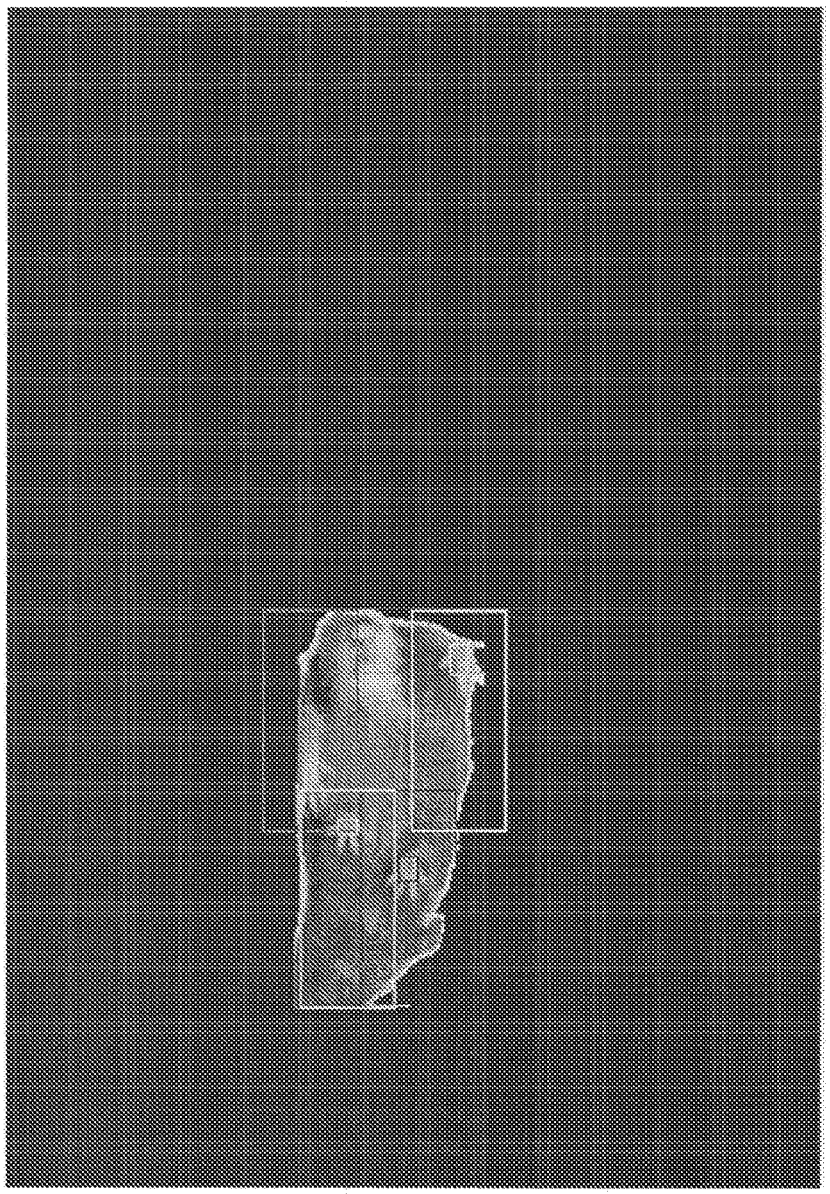
FIG. 7B illustrates the extracted foreground object with its feet identified with small rectangular boxes surrounding the detected feet.
Figure 7C:
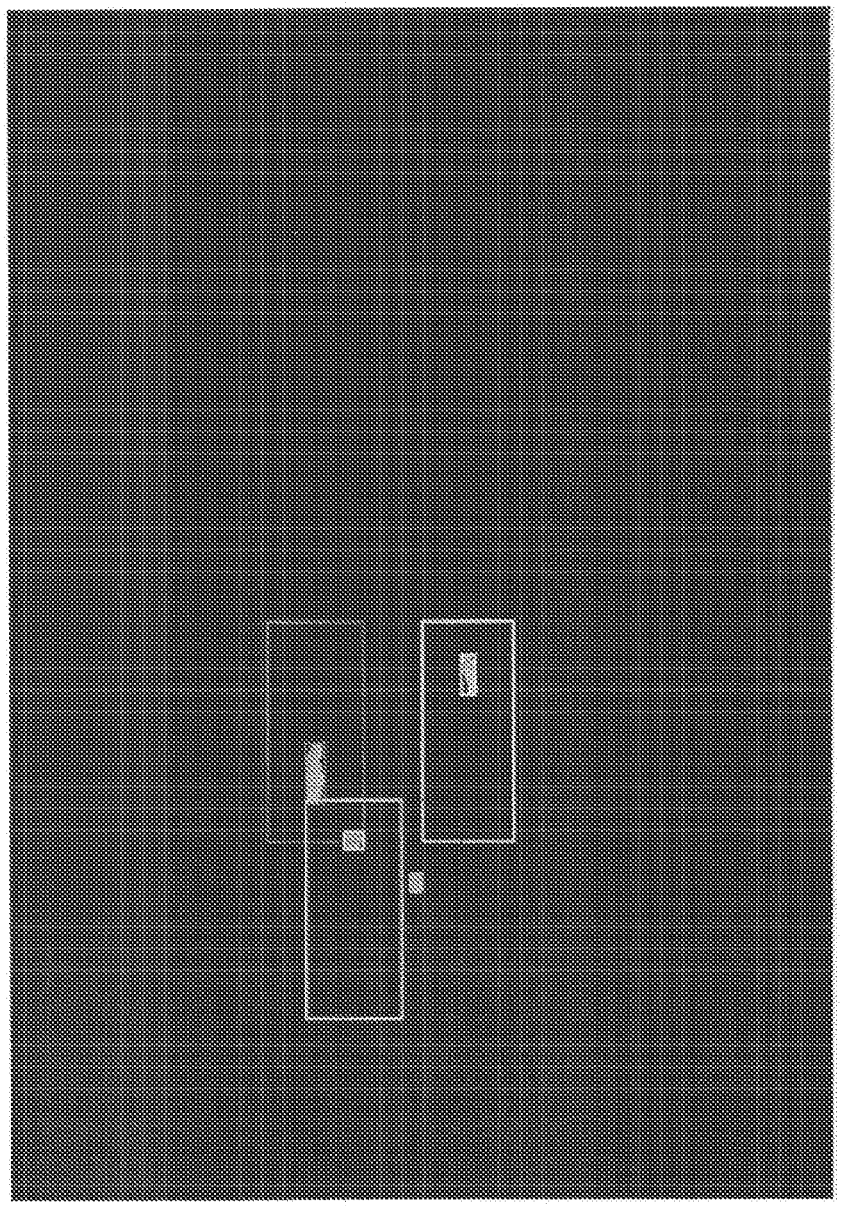
FIG. 7C shows only the detected feet with the bounding boxes. The larger bounding boxes represent the predictive area where the next occurrence of the same foot may be found.
Figure 7D:
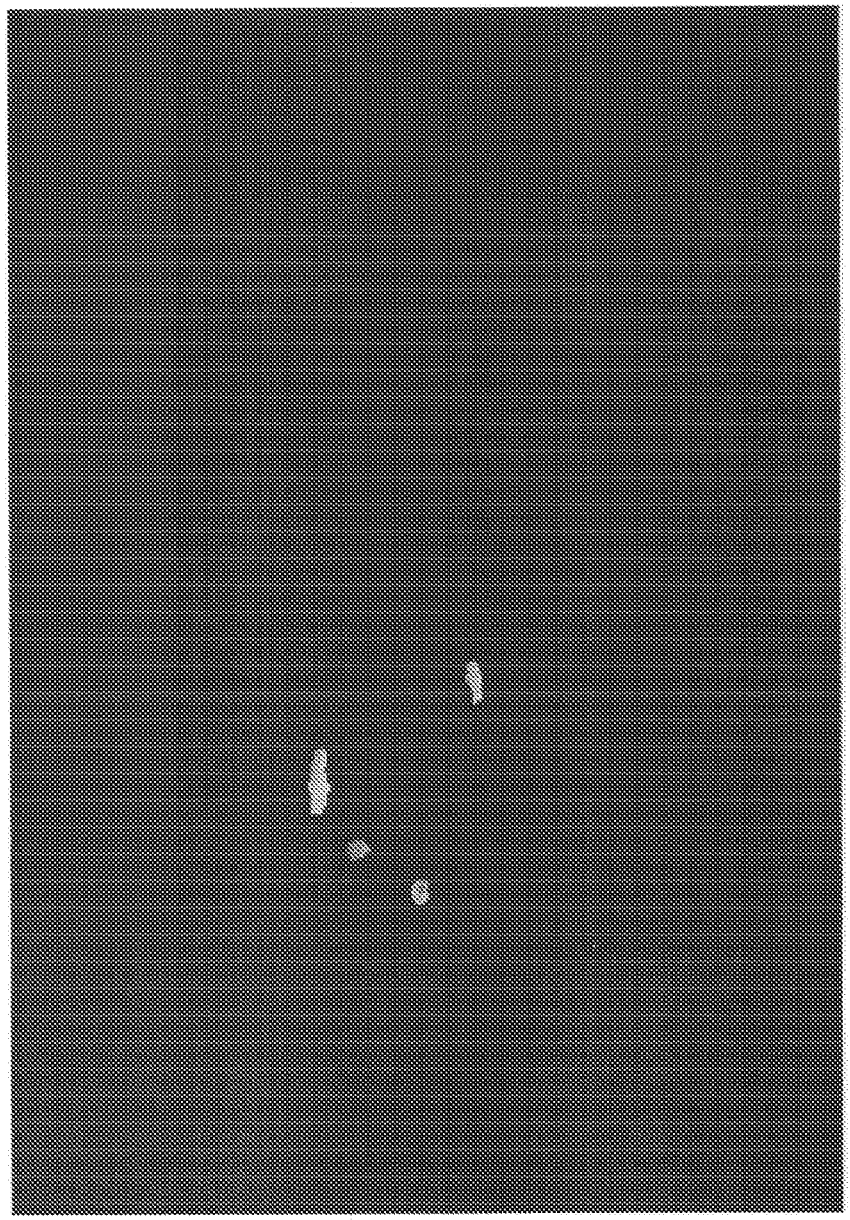
FIG. 7D shows only the detected feet without the boxes. It depicts how cleanly the feet and only the feet are detected.

FIG. 7A shows another original image and FIG. 7B shows the extracted full body. FIG. 7B also shows 4 small boxes surrounding the 4 feet of the detected animal. The 4 larger boxes represented the prediction area for the tracking to be described next. FIG. 7C shows the 4 feet only with their respective, while 7D shows the detected feet only without the boxes. These feet were detected using color models that were pre-trained from similar videos.

FIG. 8 shows an exemplary apparatus—a treadmill with a transparent tread allowing the bottom-view to be reflected on to the side to a camera. The treadmill is made up of a frame 805 that contains a receptacle 810 inside which the subject 815 to be studied is placed. The treadmill is activated and the transparent tread 820 moves causing the subject to walk or run. The tilted mirror 825 placed between the tread loop reflects the bottom-view image 830 on to the side which in turn is captured by the high-speed camera 835. The video captured by the camera is passed on to the computer for analysis by the software.

III. Foot Tracking

Ideal tracking of the feet in the image involves a matching operation to be performed that identifies corresponding points from one frame to the next. If all the points in the feet are tested for matching, this process may become computationally too consuming or expensive to perform in an efficient manner. Thus, one approach is to use approximations to the ideal case that can be accomplished in a short amount of time. For example, tracking the foreground object may be achieved by merely tracking the bounding box from one frame to the next.

When there are overlaps in foot regions from the previous frame and the current frame, this detected foot in the current frame is matched with the track of the corresponding foot from the previous frame and this foot's history is updated with all the features such as size, shape, and position. The shape features include but not limited to centroid, the principal orientation angle of the foot, the area (number of pixels), the eccentricity (roundness), and the aspect ratio of foot.

When there is no overlap, a predictive area around the previous known location of the foot is used to find the next occurrence of a foot inside this predictive area. When a foot appears in the predictive area, the tracking is resumed. Usually, the only times when tracking is lost is when the foot is in the air during the swing phase of a stride. This in no way affects any of the calculation of the gait parameters, to be described next.

A history of the bounding box position and size of each foot is maintained over the course of the analysis, and all gait parameters are calculated from these history data.

IV. Gait Parameter Calculation

Various parameters can be calculated from the historical position and size of the feet. Each of the calculated parameters are described below. Scientists can use these calculated parameters in assessing the nature of the gait behaviors of the subject animal. Some basic definitions need to be presented first. A any given time, a foot is either in a stance position or in a swing position. A stance is the first part of a stride and is defined as the backward motion of the foot while it is in contact with the floor. A swing is the forward motion of the foot to start the next stance. A stance and a swing pair constitute a stride. A stance starts the moment it touches the ground and it ends the moment it leaves the ground for the swing phase. A swing start the instant the stance ends and the swing ends when the foot regains contact with the floor to start the next stance.

A. Stride Time

The stride time is the time elapsed between two successive initiations of stances. It is sum of stance time and swing time.

B. Stride Length

In the treadmill environment, the stride length is the distance the tread has moved while the foot remains in contact with the tread.

C. Stance Time

The stance time is the time elapsed while the foot is in contact with the tread.

D. Swing Time

The swing time is the time elapsed while the foot is in the air.

E. Brake Time

In a normal stance, the size of the foot area while the foot is in contact with the floor first increases, reaches a peak, and decreases until it leaves the floor. The brake time is the time elapsed between the start of a stance and the instance the size of the foot reaches its maximum during a stance.

F. Propulsion Time

The propulsion time is the time elapsed between the instance the foot reaches maximum size in area on the floor and the time when it leaves the floor surface.

G. Instantaneous Running Speed

The instantaneous running speed of a stride is the ratio of the stride length to the stance time.

H. Average Running Speed

The average running speed is the average of all the instantaneous running speeds of strides.

I. Stride Frequency

The stride frequency is the ratio of the number of strides to the sum of the stride times of these strides.

J. Front Track Width

The front track width is the distance between the midpoint of the trajectory of the front left foot stance and the midpoint of the trajectory of the front right foot stance.

K. Rear Track Width

The rear track width is the distance between the midpoint of the trajectory of the rear left foot stance and the midpoint of the trajectory of the rear right foot stance.

L. Left Foot Base

The left foot base is the distance between the midpoint of the trajectory of the front left foot stance and the midpoint of the trajectory of the rear left foot stance.

M. Right Foot Base

The right foot base is the distance between the midpoint of the trajectory of the front right foot stance and the midpoint of the trajectory of the rear right foot stance.

N. Homologous Coupling

Homologous coupling parameter is the fraction of the stride of a given foot, when the other foot on the same half (front half or rear half) starts its stride.

O. Homolateral Coupling

Homolateral coupling parameter is the fraction of the stride of a given foot, when the other foot on the same side (left side or right side) starts its stride.

P. Diagonal Coupling

Diagonal coupling parameter is the fraction of the stride of a given foot, when the other foot diagonally opposite to the reference foot starts its stride.

Although the above exemplary embodiment is directed to a rodent analyzed in a treadmill, it is to be understood that the rodent (or any object) may be analyzed in any location or environment. Other detailed activities such as skilled reaching and forelimb movements can also be detected and characterized.

In summary, when a new video clip is analyzed, the system of the present invention first identifies the foreground object. Then, body parts such as the feet are extracted from the foreground objects, which are in turn tracked over time. These tracks of the individual feet are used to calculate the gait parameters. The image resolution of the system that has been obtained and the accuracy of calculation of the gait parameters attempted so far have been very good and resulted in an effective automated video-based gait analysis system.

The techniques developed with the present invention for automation of the gait analysis process is a powerful tool for detecting neurological and neurodegenerative effects of diseases, conditions, drugs, and gene manipulations. As previously discussed, this technology is extendable to other behavior studies of animals and humans, as well as surveillance purposes. In any case, the present invention has proven to be a significant achievement in creating an automated system and methods for automated accurate gait analysis an object whose bottom-view image is captured in a video image.

In another preferred embodiment of the invention, there are multiple cameras taking video images of experiment apparatus that contain animals. There is at least one apparatus, but, as many as the computer computing power allows, say four (4) or sixteen (16) or even more, can be analyzed. Each apparatus contains at least one animal or multiple animals. The single or multiple cameras may be taking video from different points of views such as one taking video images from the side of the apparatus, or one taking video images from underneath the apparatus. These apparatus can be treadmills or other experiment devices that allows visibility of the feet. When video images are taken of multiple apparatuses and devices containing one or multiple animals, and are analyzed for identifying these animals' behaviors, high throughput screening is achieved. When video images taken from different points of views, for example, one from the bottom view and another from the side view, are combined to identify animal's behaviors, integrated analysis is achieved.

The systematically developed definitions of gait behaviors that are detectable by the automated gait analysis system according to the present invention makes precise and quantitative analysis of the gait activity possible for the first time. The various computer algorithms included in the invention for automating gait analysis ensure accurate and efficient calculation of gait parameters. In addition, the digital video analysis techniques of the present invention improves analysis of behavior by leading to: (1) decreased variance due to non-disturbed observation of the animal; (2) increased experiment sensitivity due to the greater number of behaviors sampled over a much longer time span than ever before possible; and (3) the potential to be applied to all common normative behavior patterns, capability to assess subtle behavioral states, and detection of changes of behavior patterns in addition to individual behaviors.

Although particular embodiments of the present invention have been shown and described, it will be understood that it is not intended to limit the invention to the preferred or disclosed embodiments, and it will be obvious to those skilled in the art that various changes and modifications may be made without departing from the spirit and scope of the present invention. Thus, the invention is intended to cover alternatives, modifications, and equivalents, which may be included within the spirit and scope of the invention as defined by the claims.

For example, the present invention may also include audio analysis and/or multiple camera analysis. The video image analysis may be augmented with audio analysis since audio is typically included with most video systems today. As such, audio may be an additional variable used to determine and classify a particular objects behavior. Further, in another variation, the analysis may be expanded to video image analysis of multiple objects, for example mice, and their social interaction with one another. In a still further variation, the system may include multiple cameras providing one or more planes of view of an object to be analyzed. In an even further variation, the camera may be located in remote locations and the video images sent via the Internet for analysis by a server at another site. In fact, the foot color models may be housed in a remote location and the data files may be downloaded to a stand alone analysis system via the Internet, in accordance with the present invention. These additional features/functions add versatility to the present invention and may improve the gait analysis capabilities of the present invention to achieve gait analysis which is nearly perfect to that of a human observer for a broad spectrum of applications.

All publications, patents, and patent applications cited herein are hereby incorporated by reference in their entirety for all purposes.

What is claimed is:

1. An animal gait analysis system, comprising:
a computer configured
to determine a shape of at least one animal and position and shape of the animal's feet from a plurality of images whether or not the feet are in contact with the floor, wherein the images are images of a bottom view of the at least one animal through a transparent floor of an arena; and
to characterize activity of the animal at least in part based on analysis of the shape of the animal and the position and shape of the feet.

2. The system of claim 1, further comprising:
a video camera for capturing the images and a video digitization unit coupled to said computer for converting said images from analog to digital format if the images are captured in analog format.

3. The system of claim 1, further comprising:
an animal identification and segregation module receiving said images and identifying and segregating the animal.

4. The system of claim 3, wherein said computer further comprises a foot identification module for segregating said feet from said animal.

5. The system of claim 4, wherein said computer further comprises a foot tracking module for tracking each foot independently.

6. The system of claim 5, wherein said computer further comprises a gait characterization module for extracting gait parameters from the tracked feet.

7. The system of claim 1, wherein said animal is a mouse.

8. The system of claim 1, wherein said animal is a rat.

9. A method of analyzing gait activity of at least one animal using computer processing of images, comprising:
acquiring a plurality of images of a bottom view of the animal through a transparent floor of an arena;
analyzing the shape of the animal in said images;
identifying all feet of the animal over a plurality of said images;
determining the motion of each foot independently whether or not the feet are in contact with the floor of the arena;
calculating gait parameters of the animal based on the motion of the feet; and
characterizing gait activity of said animal based on the gait parameters.

10. The method of claim 9, wherein calculating gait parameters of the animal further comprises at least one of the following steps:
calculating the stride length and stride time;
calculating the stance and swing times;
calculating the brake and propulsion times of the stance;
calculating the average and instantaneous running speeds;
calculating the foot spacing information; and
calculating the coupling parameters of the feet.

11. The method of claim 9, wherein said analyzing the shape of the animal comprises using a background subtraction method comprising:
applying a threshold on a difference between a current image and a background so as to determine a foreground object;
refining contours of said foreground object image by smoothing to obtain the final image of the animal.

12. The method of claim 9, wherein
identifying all feet of the detected animal comprises using absolute and normalized natural color of the feet to model the feet and using the color models to identify the feet from the rest of the animal.

13. The method of claim 12, wherein identifying all feet of the animal further comprises using statistical shape and relative position information of the feet to assign correspondences for each of the feet in a current image to the instances of the feet from previous images.

14. The method of claim 9, wherein determining the motion of individual feet comprises following successive correspondences from one image to the next and maintaining a list of tracked position and shape data over the course of a sequence of images.

15. The method of claim 9, wherein the images are captured under various types of light conditions including visible, colored and infra-red light.

16. The method of claim 9, wherein the images are captured with the animals in a plurality of cages or arenas, each of which contains a single animal.

17. The method of claim 9, wherein the images are captured with high-speed cameras with speeds of up to 200 frames per second.

18. The method of claim 9, further comprising detecting body parts of the animal.

19. The method of claim 18, further comprising detecting the head of the animal.

20. The method of claim 18, further comprising detecting the tail of the animal.

21. The method of claim 18, further comprising detecting feet of the animal.

22. The system of claim 1 further comprising at least one animal behavioral gait analysis apparatus.

23. The system of claim 22, wherein said animal behavioral analysis apparatus is a movable belt apparatus with a transparent belt.

24. The system of claim 23, wherein the images are captured using a high-speed camera placed below the transparent belt so that the bottom view of the animal on the transparent belt is visible.

25. The system of claim 23, wherein said animal behavioral analysis apparatus comprises a tilted mirror placed underneath the transparent belt so that the bottom view of the animal on said transparent belt is reflected to the side where a high-speed camera is placed to capture the images.

26. The method of claim 10, wherein calculating the stride length comprises calculating a distance between an initiation of contact with the tread and a release of contact with the tread between which the foot remains in continuous contact with the tread.

27. The method of claim 10, wherein calculating the stride time comprises calculating the time elapsed between two successive initiations of contact.

28. The method of claim 10, wherein calculating the stance time comprises calculating the time elapsed between initiation and release of contact.

29. The method of claim 10, wherein calculating the swing time comprises calculating the time elapsed between release of contact of one stride and initiation of contact of the successive stride.

30. The method of claim 10, wherein calculating the brake time comprises calculating the time elapsed between an initiation of one stride and an instance when the area of the foot reaches maximum.

31. The method of claim 10, wherein calculating the propulsion time comprises calculating the time elapsed between an instance when the area of the foot reaches maximum during a stance and the release.

32. The method of claim 10, wherein calculating the instantaneous running speed comprises calculating the ratio of the stride length and the stance time, and calculating average running speed comprises calculating the average of the instantaneous running speed over the sequence of images.

33. The method of claim 10, wherein calculating the foot spacing information comprises calculating the distance between midpoints of the strides of following four pairs of feet:

front left foot and front right foot;

rear left foot and rear right foot;

front left foot and rear left foot; and front right foot and rear right foot.

34. The method of claim 10, wherein calculating the coupling parameters of the feet includes the relative offset expressed as a percentage, of the initiation of the maximum area of the other three feet with respect to the stride of the reference foot.

35. An animal gait analysis system, comprising
a computer configured to
analyze a plurality of images of at least one animal, wherein the images are images of a bottom view of the animal through a transparent movable belt of a treadmill apparatus;
determine the motion of at least one foot of the animal whether or not the foot is in contact with the transparent belt;
characterize activity of the animal based at least in part on analysis of the motion of the feet.

36. The system of claim 35, further comprising:
a video camera for capturing the images and a video digitization unit coupled to the computer for converting the images from analog to digital format if the images are captured in analog format.

37. The system of claim 35, further comprising:
an animal identification and segregation module receiving the images and identifying and segregating the animal.

38. The system of claim 37, wherein the computer further comprises a foot identification module for segregating the feet from the animal.

39. The system of claim 38, wherein the computer further comprises a foot tracking module for tracking each foot independently.

40. The system of claim 39, wherein the computer further comprises a gait characterization module for extracting gait parameters from the tracked feet.

41. The system of claim 35, wherein the animal is a mouse.

42. The system of claim 35, wherein the animal is a rat.

43. The system of claim 1 wherein the arena is a treadmill apparatus including a transparent movable belt; and wherein the transparent floor is the transparent movable belt.

44. The method of claim 9 wherein the arena is a treadmill apparatus including a transparent movable belt; and wherein the transparent floor is the transparent movable belt.

* * * * *